(12) United States Patent
Miao

(10) Patent No.: US 11,813,102 B2
(45) Date of Patent: Nov. 14, 2023

(54) INTERFEROMETER FOR X-RAY PHASE CONTRAST IMAGING

(71) Applicant: Houxun Miao, Zionsville, IN (US)

(72) Inventor: Houxun Miao, Zionsville, IN (US)

( * ) Notice: Subject to any disclaimer, the term of this patent is extended or adjusted under 35 U.S.C. 154(b) by 126 days.

(21) Appl. No.: 17/450,085

(22) Filed: Oct. 6, 2021

(65) Prior Publication Data

US 2023/0104855 A1 Apr. 6, 2023

(51) Int. Cl.
*A61B 6/00* (2006.01)
*G21K 1/06* (2006.01)

(52) U.S. Cl.
CPC ............ *A61B 6/484* (2013.01); *A61B 6/4021* (2013.01); *A61B 6/4035* (2013.01); *A61B 6/4291* (2013.01); *G21K 1/062* (2013.01); *G21K 1/065* (2013.01); *G21K 2201/061* (2013.01); *G21K 2201/062* (2013.01); *G21K 2201/067* (2013.01); *G21K 2207/005* (2013.01)

(58) Field of Classification Search
None
See application file for complete search history.

(56) References Cited

U.S. PATENT DOCUMENTS

| 7,180,979 | B2 * | 2/2007 | Momose | G21K 1/06 |
| | | | | 378/70 |
| 7,889,838 | B2 * | 2/2011 | David | A61B 6/4233 |
| | | | | 378/36 |
| 9,348,067 | B2 * | 5/2016 | Vogtmeier | G02B 5/1857 |
| 9,532,760 | B2 * | 1/2017 | Anton | A61B 6/4291 |
| 9,719,947 | B2 * | 8/2017 | Yun | G01N 23/20075 |
| 9,763,634 | B2 * | 9/2017 | Preusche | A61B 6/484 |
| 9,881,710 | B2 * | 1/2018 | Roessl | G21K 1/06 |
| 2005/0286680 | A1 * | 12/2005 | Momose | G01N 23/041 |
| | | | | 378/62 |
| 2009/0092227 | A1 * | 4/2009 | David | A61B 6/484 |
| | | | | 378/36 |
| 2012/0020461 | A1 * | 1/2012 | Roessl | G21K 1/06 |
| | | | | 378/87 |
| 2012/0057677 | A1 * | 3/2012 | Vogtmeier | G02B 5/1857 |
| | | | | 359/569 |

(Continued)

FOREIGN PATENT DOCUMENTS

| EP | 1447046 A1 * | 8/2004 | ............... A61B 6/00 |
| EP | 3139156 A1 * | 3/2017 | ............... A61B 6/484 |

(Continued)

OTHER PUBLICATIONS

Arboleda, C., et al. "Towards clinical grating-interferometry mammography." European radiology 30.3 (2020): 1419-1425.*

(Continued)

*Primary Examiner* — Thomas R Artman

(57) ABSTRACT

Disclosed herein is an x-ray interferometer for x-ray phase contrast imaging including an x-ray source, an x-ray source grating, two x-ray phase gratings, an x-ray analyzer grating and an x-ray detector. An alternative interferometer includes a periodically structured x-ray source, two x-ray phase gratings, an x-ray analyzer grating and an x-ray detector. The phase gratings are placed much closer to the x-ray detector than to the x-ray source and the image object is positioned upstream and close to the phase gratings to achieve high sensitivity and large field-of-view simultaneously.

11 Claims, 6 Drawing Sheets

(56) References Cited

U.S. PATENT DOCUMENTS

| | | | | |
|---|---|---|---|---|
| 2015/0055744 A1* | 2/2015 | Anton | ............... | A61B 6/484 |
| | | | | 378/36 |
| 2015/0243397 A1* | 8/2015 | Yun | ............... | A61B 6/484 |
| | | | | 378/36 |
| 2016/0066873 A1* | 3/2016 | Preusche | ............ | A61B 6/4233 |
| | | | | 378/36 |

FOREIGN PATENT DOCUMENTS

| | | | | | |
|---|---|---|---|---|---|
| RU | | 2584247 C2 * | 5/2016 | ............ | G01N 23/04 |
| RU | | 2666153 C2 * | 9/2018 | ............ | G21K 1/06 |
| WO | WO-2010150136 A1 * | | 12/2010 | ............ | A61B 6/032 |
| WO | WO-2013160153 A1 * | | 10/2013 | ........... | A61B 6/4291 |

OTHER PUBLICATIONS

Fingerle, A. A., et al. "Imaging features in post-mortem x-ray dark-field chest radiographs and correlation with conventional x-ray and CT." European radiology experimental 3.1 (2019): 25.*

* cited by examiner

INTERFEROMETER FOR X-RAY PHASE CONTRAST IMAGING

CROSS REFERENCE TO RELATED APPLICATIONS

N/A

FIELD

The present invention relates to an x-ray interferometer with an x-ray source, x-ray gratings and an x-ray detector for x-ray phase contrast imaging. More specifically, the invention relates to an x-ray interferometer that achieves high sensitivity and large field of view with less critical requirements on the small period and high aspect ratio x-ray analyzer (absorption) grating as in a Talbot-Lau interferometer of similar performance.

BACKGROUND

X-ray imaging has been used for medical diagnosis for more than a hundred years. X-ray phase contrast imaging, detecting the phase and the dark-field contrasts in addition to the absorption, has the potential to improve both the sensitivity and specificity of medical diagnosis by joint analysis of the three contrast mechanisms. Recent preclinical studies in breast imaging [Arboleda, C., et al. "Towards clinical grating-interferometry mammography." European radiology 30.3 (2020): 1419-1425] and lung imaging [Fingerle, A. A., et al. "Imaging features in post-mortem x-ray dark-field chest radiographs and correlation with conventional x-ray and CT." European radiology experimental 3.1 (2019): 25] demonstrate the potential clinical values of x-ray phase contrast imaging in breast imaging and lung imaging.

For daily clinical operation, the x-ray phase contrast imaging system has to be constructed with polychromatic x-ray tubes and large area medical x-ray detectors (e. g. 29 cm×24 cm for digital mammography, 43 cm×35 cm for chest x-rays) with much lower spatial resolution compared to the period of the x-ray gratings. In prior arts, the U.S. Pat. No. 7,180,979B2 describes a Talbot interferometer, utilizing the Talbot self-imaging of an x-ray phase grating to allow the use of polychromatic x-ray sources. To resolve the fine pitch of the self-imaging pattern, an absorption grating with similar period as the self-image of the phase grating is placed in front of the detector and the resulting moiré fringe is recorded by the detector, which is compatible with medical x-ray detectors with low spatial resolution. A phase stepping method is described to retrieve the absorption contrast, phase contrast and dark-field contrast images at the detector spatial resolution. For Talbot self-imaging phenomena, the source has to have sufficient spatial coherence (at least half the grating period at the phase grating), which requires synchrotron x-ray source or at least microfocus source. The U.S. Pat. No. 7,889,838B2 describes a Talbot-Lau interferometer to release the spatial coherence requirements of the x-ray source. Compared to Talbot interferometer in U.S. Pat. No. 7,180,979B2, an absorption grating is placed downstream the x-ray source. The combination of the low spatial coherence x-ray source and the source grating is equivalent to an array of line sources. Each line source provides sufficient spatial coherence for Talbot self-imaging of the phase grating. Under certain source grating period, the Talbot self-imaging of the phase grating from each line source is aligned in phase and added up (in intensity) constructively, although the line sources are spatially incoherent with each other. The combination of the low coherence x-ray source and the source grating can be replaced by a micro-structured x-ray source, providing an array of equally spaced sources, with a period satisfying Talbot-Lau condition as described in U.S. Pat. No. 7,889,838B2 and U.S. Pat. No. 9,719,947B2.

The maximum interferometer sensitivity of a Talbot-Lau interferometer is proportional to the distance between the phase grating and the analyzer grating and inversely proportional to the period of the analyzer grating. The interferometer sensitivity at the image object is a fraction of the maximum sensitivity. If the image object is placed upstream the phase grating, the fractional factor is the ratio of the distance between the source grating and the image object to the distance between the source grating and the phase grating. If the image object is placed downstream the phase grating, the fractional factor is the ratio of the distance between the image object and the analyzer grating to the distance between the phase grating and the analyzer grating. For a given x-ray imaging application, assuming sufficiently large gratings to cover the entire x-ray detector, the field of view is a fraction of the detector area, where the fractional factor is the square of the ratio of the distance between the x-ray source and the image object to the source-to-detector distance. For clinical diagnoses, such as digital mammography and chest x-ray radiography, to achieve large field of view, the patient position has to be close to the detector. Under the patient to detector distance and source-to-detector distance restrictions, the period of the analyzer grating has to be sufficiently small to get high interferometer sensitivity. Since a thick layer of high atomic number material (e. g. 50 μm Au for 30 keV x-rays and 200 μm Au for 60 keV x-rays) is required to sufficiently absorb hard x-ray photons, high aspect ratio x-ray gratings are necessary in Talbot-Lau interferometer to achieve compact, highly sensitive x-ray phase contrast imaging system. Fabrication of the small period and high aspect ratio analyzer gratings is a major challenge in the development of Talbot-Lau interferometers for clinical applications.

Analyzer grating free x-ray interferometers have been developed, including an x-ray polychromatic far field interferometer with 3 phase gratings [Miao, H., et al. "A universal moiré effect and application in X-ray phase-contrast imaging." Nature physics 12.9 (2016): 830-834] and dual phase grating x-ray interferometers [Kagias, M., et al. "Dual phase grating interferometer for tunable dark-field sensitivity." Applied Physics Letters 110.1 (2017): 014105. Yan, A., Wu, X., and Liu, H. "Quantitative theory of x-ray interferometers based on dual phase grating: fringe period and visibility." Optics Express 26.18 (2018): 23142-23155. Ge, Y., et al. "Dual phase grating based X-ray differential phase contrast imaging with source grating: theory and validation." Optics Express 28.7 (2020): 9786-9801.]. Although, the sensitivity of the 3-grating polychromatic far field interferometer is the highest among all reported grating-based interferometers, the large distance required between the detector and the grating next to the detector and the large inter-grating distances makes the field of view small. Moreover, the intrinsic fringe period of such an interferometer is typically not resolvable by medical x-ray detectors. The small field of view together with the incompatibility with large area medical x-ray detectors limits its clinical potential, particularly for full field imaging such as in applications of breast imaging and chest radiography. The dual-phase grating x-ray interferometers suffer from small fringe period that cannot be resolved by large area medical detectors, small focal spot requirement of the x-ray source, and the low interferometer sensitivity. These drawbacks make it difficult to develop a practical imaging system for clinical diagnosis.

SUMMARY

This disclosure provides an x-ray phase contrast imaging system using an analyzer grating of much larger period and lower aspect ratio than that used in a Talbot-Lau interferometer of similar performance. The system is compatible with polychromatic, low spatial coherence medical x-ray tubes and large area medical x-ray detectors for large field of view imaging, which is required for applications, such as in lung imaging, breast imaging and abdomen imaging.

The system consists of
a) A standard polychromatic medical x-ray source.
b) A source grating (x-ray absorption grating) with period $p_s$ placed downstream and close to the x-ray source.
c) Two x-ray phase gratings with period $p_1$ and $p_2$ and an inter-grating distance of D. The grating period $p_1$ and $p_2$ can be selected the same or different. The gratings are placed closer to the detector than the x-ray source. The phase shifts of the two gratings are typically selected to be different and can be individually optimized between a fraction of $\pi$ to multiple $\pi$. The grating profiles can also be independently optimized to maximize the interferometer fringe visibility.
d) An analyzer grating (x-ray absorption grating) with period $p_a$, placed in front of the x-ray detector.
e) A standard large area medical x-ray detector.

The combination of a standard polychromatic medical x-ray source and the source grating can be replaced by a periodically structured x-ray source. An alternative system consists of
a) A periodically structured x-ray source with a period of $p_s$.
b) Two x-ray phase gratings with period $p_1$ and $p_2$ and an inter-grating distance of D.
c) An analyzer grating (x-ray absorption grating) with period $p_a$, placed in front of the x-ray detector.
d) A standard large area medical x-ray detector.

The two x-ray phase gratings form a universal moiré pattern at the plane of the analyzer grating. The period of the analyzer grating is selected to convert the universal moiré pattern to lower spatial frequency fringe via intensity moiré effect. The resulted intensity moiré pattern can be resolvable by the x-ray detector, which requires a period of at least 3 times the detector spatial resolution, preferably ≥5 times the detector resolution.

The spatial coherence requirement of the interferometer limits the spot size of the x-ray source to a few μm or a few tens of μm. X-ray microfocus source cannot meet the requirement of small focal spot size and high output power at the same time for fast data acquisition. This is solved in this disclosure by using either a source grating (absorption grating) placed downstream and close to the x-ray source or a periodically structured x-ray source. The source grating converts the x-ray source to a group of line sources, where the coherence of each line source meets the coherence requirement. To achieve high fringe visibility, the source period is selected such that the universal moiré pattern formed by each individual source adds up constructively.

The image object is designed to be placed upstream and close to the two phase gratings. The interferometer sensitivity is proportional to the distance between the source grating (or structured source) and the image object, and inversely proportional to the source period ($p_s$). The two phase gratings are placed close to the analyzer grating and the detector to simultaneously increase the interferometer sensitivity and the field of view. A certain distance between the phase gratings and the analyzer grating is required to achieve high fringe visibility. When the two phase gratings are selected to have the same period, the source and the analyzer gratings have the same period. Alternatively, the two phase gratings can be selected to have different periods to reduce the source period and increase the analyzer grating period. Decreased source grating period improves the interferometer sensitivity. In some applications, the analyzer grating period can be increased large enough to allow the use of large area x-ray grid made of lead to simplify the instrumentation and reduce the cost.

BRIEF DESCRIPTION OF THE DRAWINGS

The embodiments of the present invention will become better understood with reference to the following drawings. It is noted that, for purpose of illustrative clarity, certain elements in various drawings may not be drawn to scale. These drawings depict exemplary embodiments of the disclosure, but should not be considered to limit its scope. Preferred examples and embodiments are described hereinafter with reference to the accompanying drawings, wherein.

DETAILED DESCRIPTION

Various embodiments of the disclosure are discussed in details below. While specific implementations are discussed, it should be understood that this is done for illustration purposes only. A person skilled in the relevant art will recognize that other components and configurations may be used without parting from the spirit and scope of the disclosure. Thus, the following description, drawings and examples are illustrative and are not to be construed as limiting.

Figure 1:
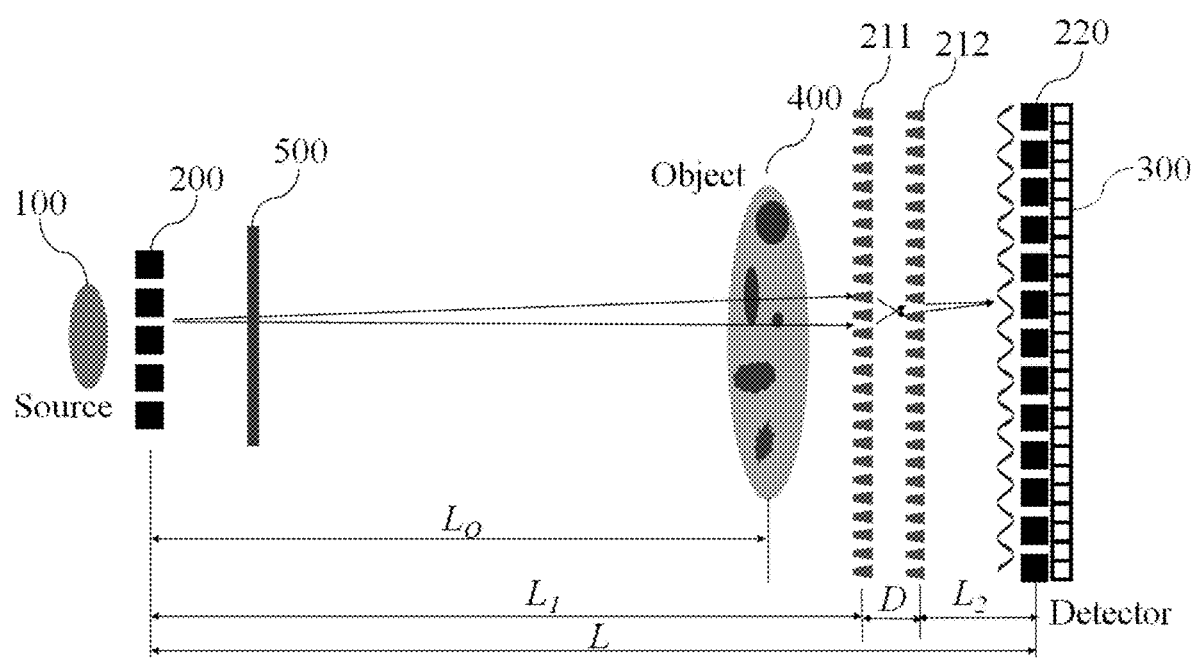
FIG. 1 is a schematic illustration of an x-ray interferometer consisting of a polychromatic, low spatial coherence medical x-ray tube, a source grating, an optional filter, two phase gratings, an analyzer grating, and a medical x-ray detector, according to an embodiment of the present invention.

In a first embodiment of the present invention, the x-ray interferometer is constituted by a medical x-ray source 100, an x-ray absorption grating called a source grating 200, a first x-ray phase grating 211, a second x-ray phase grating 212, an x-ray absorption grating called an analyzer grating 220, and an x-ray detector 300 (refer to FIG. 1). The size of the source grating 200 is selected to be large enough to cover the cone-beam projection of the detector at the source grating plane, typically a few cm by a few cm. An optional filter 500 is placed downstream or upstream the source grating 200 to tailor the x-ray spectrum if preferred. The image object 400 is typically positioned upstream and close to the first phase grating 211. The combination of a medical x-ray source and a source grating represents an array of line sources, where the width of each individual line meets the spatial coherence requirement.

In a second embodiment, the conventional medical x-ray source and the source grating is replaced by a structures x-ray source 100-SS (Refer to FIG. 2), while all the other components are the same as in the first embodiment illustrated in FIG. 1.

The x-ray source 100 (Refer to FIG. 1) is a typical medical x-ray source for a specific application, for example, a rotating anode x-ray source. The source grating 200 (Refer to FIG. 1) is an x-ray absorption grating, consisting of a low x-ray absorption substrate 201, a group of low absorption grating teeth 202 and a group of high absorption grating teeth 203 (Refer to FIG. 3). The substrate 201 is, for example, Si or other low-density materials. The low absorption grating teeth 202 are for example, Si, polymer or other low-density materials. When grating teeth 202 are Si, they can be fabricated on the Si substrate 201 via wet or dry deep Si etch. The high absorption grating teeth 203 are for example, Au, Pt or other high-density material. The shape of the grating teeth is preferred to be rectangle. Perfectly rectangular grating teeth are not practical during the fabrication process. Deviations from rectangular shape, such as curved rectangle, trapezoid, curved trapezoid, etc., and roughness on the sidewall surfaces are all acceptable, provided that periodical x-ray transmission and absorption pattern is clearly defined. The duty cycle, defined as the ratio of the low absorption grating teeth width to the grating pitch, of grating 200 is typically selected between 25% to 50%, preferably below 50%. A smaller duty cycle improves the interferometer fringe visibility at the cost of the transmitted x-ray flux. When an x-ray structured source is used (Refer to FIG. 2), the duty cycle of the source 100-SS, defined as the ratio of each individual x-ray emission element width to the pitch of the source, is typically selected between 25% to 50%, preferable below 50%.

Figure 4:
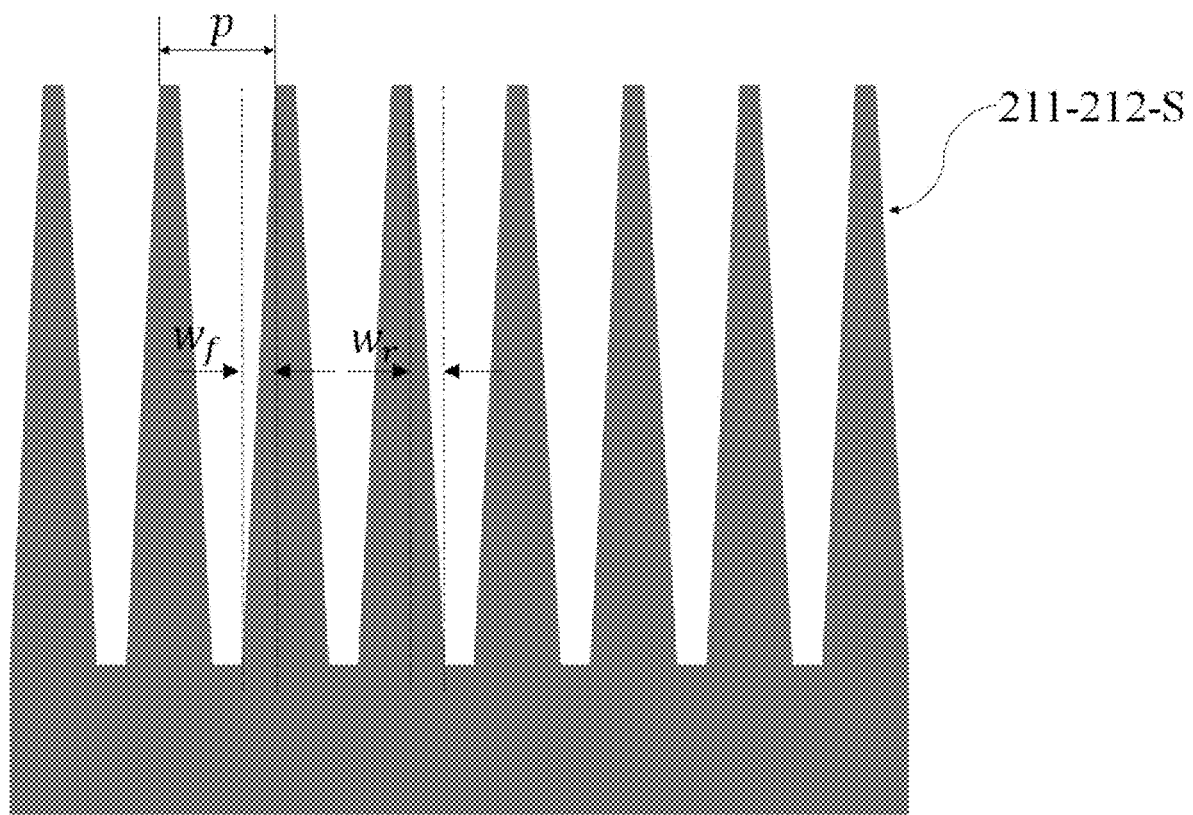
FIG. 4 is a cross-sectional illustration of a single element phase grating with trapezoid shaped grating teeth.
Figure 5:
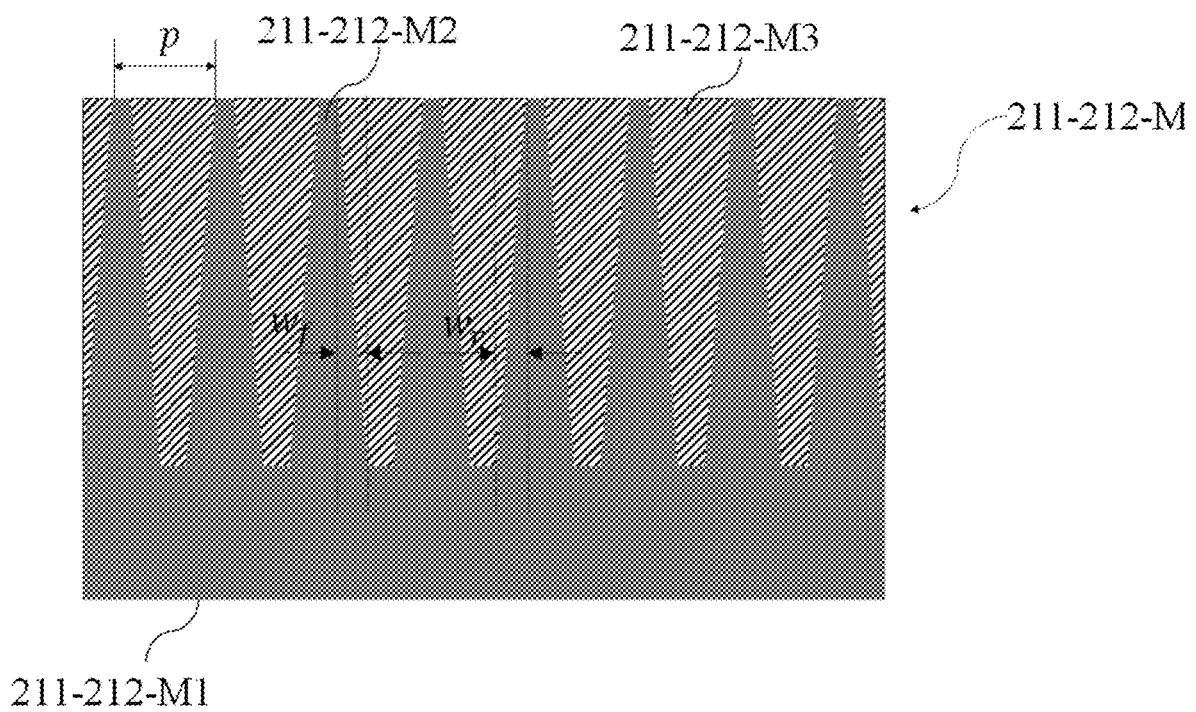
FIG. 5 is a cross-sectional illustration of a trapezoid shaped phase grating consisting of weak phase shift and strong phase shift materials.

The x-ray phase gratings 211 and 212 (Refer to FIG. 1 and FIG. 2) are typically selected to have an approximately isosceles trapezoid grating teeth. Fabrication process introduced slightly deviations from isosceles trapezoid are acceptable. A phase grating can consist of a single element (for example, a Si grating) 211-212-S(Refer to FIG. 4). A phase grating can consist of multiple materials, 211-212-M (Refer to FIG. 5), including a low x-ray absorption substrate 211-212-M1, a group of weak phase shift (phase shift refer to relative phase shift compared to air throughout the disclosure) grating teeth 211-212-M2 and a group of strong phase shift grating teeth 211-212-M3 (Refer to FIG. 5). The aspect ratio (defined as two times the ratio of the grating depth to the grating pitch) of a multiple-material phase grating is much smaller than that of a single material phase grating at the same x-ray phase shift level. The substrate 211-212-M1 is, for example, Si or other low-density materials. The week phase shift grating teeth 211-212-M2 are for example, Si, polymer or other low-density materials. The strong phase shift grating teeth 211-212-M3 are for example, nickel, gold or other high-density materials. The grating phase shift can be optimized typically in the range of a fraction of π to a few π at the central x-ray energy to maximize the interferometer fringe visibility. The intensity modulations introduced by the phase gratings, particularly when multiple-material phase gratings are used, play a role in the interferometer, typically slightly improve the fringe visibility. The multiple-material phase gratings, particularly when the phase shifts are above π, are sometimes called hybrid (phase and absorption) gratings. In this disclosure, we call such gratings as phase gratings. The average duty cycle, defined as the ratio of the average weak phase shift grating teeth width to the grating pitch (e. g. ratio of the Si teeth width to the grating pitch in a Si/Au phase grating), can be optimized in the range of 25% to 80% to maximize the interferometer fringe visibility. The width for the phase rising $w_r$ or phase falling $w_f$ (Refer to FIG. 4 and FIG. 5) can be optimized in the range of 0 to 50% the grating pitch to maximize the interferometer fringe visibility.

Figure 6:
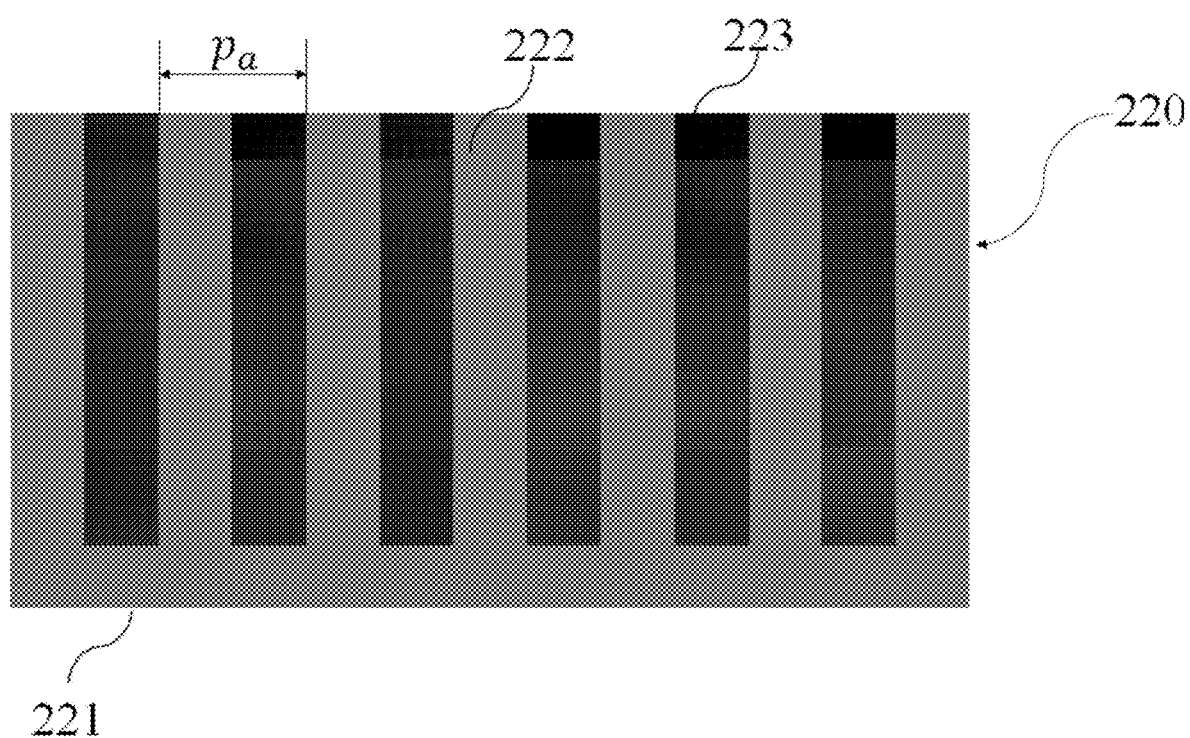
FIG. 6 is a cross-sectional illustration of the analyzer grating consisting of low absorption and high absorption materials.

The analyzer grating 220 is an x-ray absorption grating, consisting of a low x-ray absorption substrate 221, a group of low absorption grating teeth 222 and a group of high absorption grating teeth 223 (Refer to FIG. 6). The substrate 221 is, for example, Si or other low-density materials. The low absorption grating teeth 222 are for example, Si, polymer or other low-density materials. When grating teeth 222 are Si, they can be fabricated on the Si substrate 221 via wet or dry deep Si etch. The high absorption grating teeth 223 are for example, Au, Pt or other high-density materials. The shape of the grating teeth is preferred to be rectangle. Perfectly rectangular grating teeth are not practical during the fabrication process. Deviations from rectangular shape, such as curved rectangle, trapezoid, curved trapezoid, etc., and roughness on the sidewall surfaces are all acceptable, provided that periodical x-ray transmission and absorption pattern is clearly defined. The duty cycle grating 220 is typically selected to be approximately 50%.

Figure 2:
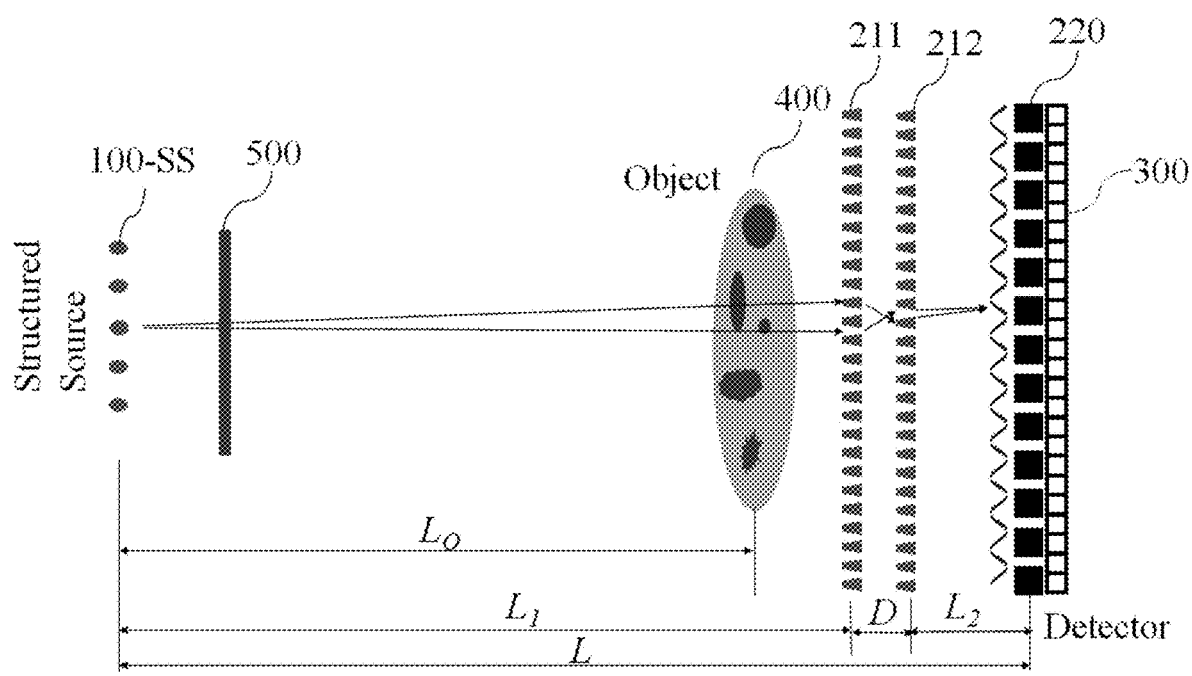
FIG. 2 is a schematic illustration of an x-ray interferometer, consisting of a structured x-ray source, an optional filter, two phase gratings, an analyzer grating and a medical x-ray detector, according to an embodiment of the present invention.
Figure 3:
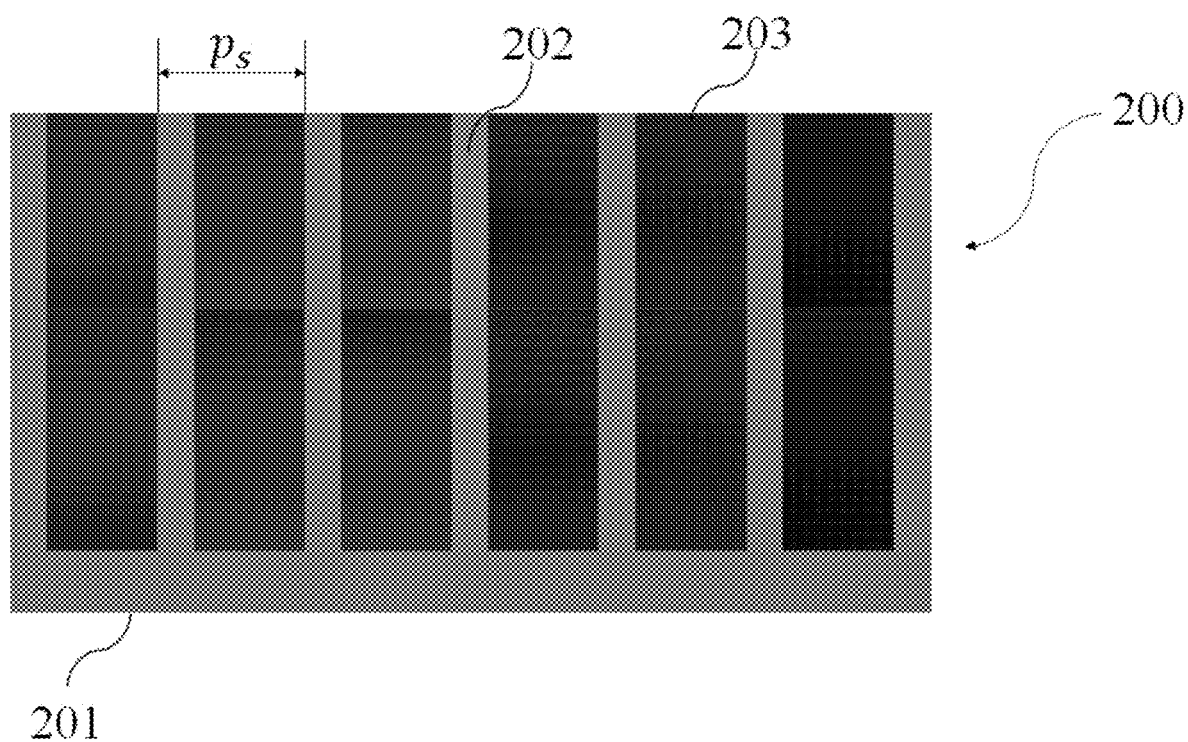
FIG. 3 is a cross-sectional illustration of the source grating consisting of low absorption and high absorption materials.

The period of the source grating 200 (Refer to FIG. 1) or the period of the structured x-ray source 100-SS (Refer to FIG. 2) is selected as:

$$p_s = \frac{p_1 p_2 L}{(p_2 - p_1)L_2 + p_2 D}.$$

Where L, $L_2$ and D are the distance from the source grating 200 or the structured source 100-SS to the analyzer grating 220, the distance from the phase grating 212 to the analyzer grating 220, and the distance between the two phase gratings 211 and 212, respectively, as illustrated in FIG. 1 and FIG. 2. $p_1$ and $p_2$ are the periods of the phase gratings 211 and 212, respectively. The source grating period can be slightly different from $p_s$ as long as the fringe visibility of the interferometer is not obviously degraded.

The period of the analyzer grating 220 (Refer to FIG. 1 and FIG. 2) is selected as:

$$p_a = \frac{p_1 p_2 L}{(p_1 - p_2)L_1 + p_1 D}.$$

Where $L_1$ is the distance from the source grating 200 or the structured source 100-SS to the phase grating 211, as illustrated in FIG. 1 and FIG. 2. The period of the analyzer grating 220 can be slightly different from $p_a$ as long as the fringe period at the detector is resolvable by the detector.

The image object 400 is designed to be upstream and close to the phase grating 211. The interferometer sensitivity at the object is $\eta = L_O/p_s$, where $L_O$ is the distance from the source grating 200 or the structured source 100-SS to the image object 400, as illustrated in FIG. 1 and FIG. 2. When the projections of the gratings cover the entire x-ray detector, the field-of-view is proportional to the distance between the x-ray source and the image object ($L_{S-O}$) and inversely proportional to the source-to-detector distance ($L_{S-D}$). When a structured x-ray source is used, the source-to-object distance and the source-to-detector distance are $L_O$ and L, respectively, as illustrated in FIG. 2. When a medical x-ray source and a source grating are used, $L_{S-O}$ and $L_{S-D}$ are not marked in FIG. 1 for simplicity, which should not cause any confusion.

For a specific application, given the source-to-detector distance restriction, the period and position of the phase gratings 211 and 212 (Refer to FIG. 1 and FIG. 2) are selected to satisfy the interferometer sensitivity and field-of-view requirements and, at the same time, to provide a high contrast universal moiré pattern at the plane of the analyzer grating. Since the field-of-view and the interferometer sensitivity both increase with the increase of the distance between the source and the image object, the phase gratings are designed to be placed closer to the detector than the x-ray source. The distance between the phase grating 211 and the source grating 200 (Refer to FIG. 1) or the structured source 100-SS (Refer to FIG. 2) is limited by the source-to-detector distance restriction and by the fringe visibility of the universal moiré pattern, which requires certain distance between the phase grating 212 and the analyzer grating 220. Using the fringe visibility of the universal moiré pattern, generated by phase gratings 211 and 212, as the figure of merit, the parameters of phase gratings 211 and 212 (periods, phase shifts and cross-sectional profiles), and their positions are globally optimized.

The embodiments of the invention are best described by application examples as described below.

EXAMPLES

Example 1: An X-Ray Interferometer for Multi-Contrast Chest X-Ray Radiography

The interferometer (Refer to FIG. 1) consists of a tungsten targeted rotating anode x-ray source 100; a 6 cm×6 cm area, 30.1 μm period, 25% duty cycle, 300 μm height Si/Au source grating 200; a 38 cm×31.5 cm area (twelve 9.5 cm×10.5 cm gratings stitched together), 900 nm period, 9 μm height Si/Au phase grating 211; a 38 cm×31.5 cm area (twelve 9.5 cm×10.5 cm gratings stitched together), 900 nm period, 12.5 μm height Si/Au phase grating 212; a 44 cm×36 cm area (sixteen 11 cm×9 cm gratings stitch together), 30.1 μm period, 50% duty cycle, 300 μm height Si/Au analyzer grating 220; and a 43 cm×35 cm direct deposit CsI x-ray flat panel detector 300. The source grating 200 is placed approximately 0.1 m downstream the focal spot of the x-ray source 100 and the analyzer grating 220 is placed approximately 0.01 m upstream the detector 300. The distances from the source grating 200 to the analyzer grating 220, from the phase grating 211 to the phase grating 212, and from the phase grating 212 to the analyzer grating 220 are L=1.907 m, D=0.057 m and $L_2$=0.25 m, respectively. The duty cycle and the phase rising (or falling) width (Refer to FIG. 4 and FIG. 5, $w_r$ or $w_f$) of grating 211 are 65% and 225 nm. The duty cycle and the phase rising (or falling) width of grating 212 are 65% and 225 nm. At 90 kVp x-ray tube operation voltage, the fringe visibility is estimated to be 20%. The maximally achievable interferometer sensitivity is $\eta$=5.3×10$^4$. The image object position is designed to be upstream and close to the phase grating 211. Assuming the image object thickness is 40 cm, the average effective interferometer sensitivity at the object is approximately 4.7×10$^4$. The field-of-view at the central plane of the image object is approximately 32 cm×26 cm. The field-of-view can be further increased by using a combination of two x-ray flat panel detectors and larger area gratings, or by scanning the interferometer across the image object.

Variations of the grating parameters from the designed values are well tolerated. A 2% fringe visibility degradation allows at least, for the source grating 200 or the analyzer grating 220, +5% variation of the duty cycle; or for the phase gratings 211 or 212, +10% variation of the grating height, or +5% variation of the duty cycle, or +20% variation of the phase rising (or falling) width.

The grating parameters can be easily controlled within the acceptable range during the grating fabrication process. In one embodiment of the grating fabrication, the source grating 200 of 30.1 μm period is fabricated by deep reactive ion etching (DRIE) of Si to 300 μm in depth. The Si grating teeth width is controlled to around 7.5 μm by controlling the grating teeth width during the lithography process and the DRIE process. The trenches are then filled with Au via electrodeposition. The phase gratings 211 and 212 of 900 nm period are patterned by i-line stepper and deep etched by DRIE of Si. By controlling the DRIE process, the grating 211 height is controlled to 9±0.9 μm, the average Si teeth width is controlled to 585±45 nm, and the phase rising (or falling) width is controlled to 225±45 nm. The grating 212 height is controlled to 12.5±1.25 μm, the average Si teeth width is controlled to 585±45 nm, and the phase rising (or falling) width is controlled to 225±45 nm. Au is deposited via electroplating to fill the trenches to complete the fabrication of phase gratings 211 and 212. The analyzer grating 220 of 30.1 μm period is fabricated by DRIE of Si to 300 μm in depth. The Si grating teeth width is controlled to around 15 μm by controlling the grating teeth width during the lithography process and the DRIE process. The trenches are then filled with Au via electrodeposition.

Example 2: An X-Ray Interferometer for Multi-Contrast Chest X-Ray Radiography Using a Lead X-Ray Grid as the Analyzer Grating Large area x-ray absorption gratings made of Au are costly. In this example, the analyzer grating period is enlarged by using two phase gratings with different period, so that a lead x-ray grid can be used as the analyzer grating. The interferometer (Refer to FIG. 1) consists of a tungsten targeted rotating anode x-ray source 100; a 6 cm×6 cm area, 33 μm period, 25% duty cycle, 300 μm height Si/Au source grating 200; a 36 cm×30 cm area (twelve 9 cm×10 cm gratings stitched together), 811 nm period, 9 μm height Si/Au phase grating 211; a 36 cm×30 cm area (twelve 9 cm×10 cm gratings stitched together), 825 nm period, 18 μm height Si/Au phase grating 212; a 43 cm×35 cm size, 230 lines per inch (or 90 lines per cm), 50% duty cycle, 2 m focal distance aluminum interspaced lead grid as the analyzer grating 220; and a 43 cm×35 cm direct deposit CsI x-ray flat panel detector 300. The source grating 200 is placed approximately 0.1 m downstream the focal spot of the x-ray source 100 and the analyzer grating 220 (lead grid) is attached to the detector 300. The distances from the source grating 200 to the analyzer grating 220, from the phase grating 211 to the phase grating 212, and from the phase grating 212 to the analyzer grating 220 are L=1.993 m, D=0.043 m and $L_2$=0.35 m, respectively. The duty cycle and the phase rising (or falling) width of grating 211 are 55% and 203 nm. The duty cycle and the phase rising (or falling) width of grating 212 are 70% and 206 nm. At 90 kVp x-ray tube operation voltage, the fringe visibility is estimated to be 19%. The maximally achievable interferometer sensitivity is η=4.8×10⁴. The image object position is designed to be upstream and close to the phase grating 211. Assuming the image object thickness of 40 cm, the average effective interferometer sensitivity at the object is approximately 4.2×10⁴. The field-of-view at the central plane of the image object is approximately 31 cm×25 cm. The field-of-view can be further increased by using a combination of two x-ray flat panel detectors and larger area gratings, or by scanning the interferometer across the image object.

A 2% fringe visibility degradation allows at least, for the source grating 200 or the analyzer grating 220, ±5% variation of the duty cycle; or for the phase gratings 211 or 212, ±10% variation of the grating height, or ±5% variation of the duty cycle, or ±20% variation of the phase rising (or falling) width. The grating parameters can easily be controlled to the tolerant range during the fabrication process.

Example 3: An x-Ray Interferometer for Multi-Contrast Breast Imaging

The interferometer (Refer to FIG. 1) consists of a tungsten target rotating anode x-ray source 100; a 6 cm×6 cm area, 5.7 µm period, 25% duty cycle, 60 µm height Si/Au source grating 200; a 24 cm×20 cm area (six 8 cm×10 cm gratings stitched together), 1.25 µm period, 4.4 µm height Si/Au phase grating 211; a 30 cm×24 cm area (nine 8 cm×10 cm gratings stitched together), 1.25 µm period, 8.8 µm height Si/Au phase grating 212; a 30 cm×24 cm area (nine 8 cm×10 cm gratings stitched together), 5.7 µm period, 50% duty cycle, 60 µm height Si/Au source grating 220; and a 29 cm×24 cm amorphous selenium x-ray flat panel detector. The source grating 200 is placed approximately 0.13 m downstream the focal spot of the x-ray source 100 and the analyzer grating 220 is placed approximately 0.01 m upstream the detector 300. The distances from the source grating 200 to the analyzer grating 220, from the phase grating 211 to the phase grating 212, and from the phase grating 212 to the analyzer grating 220 are L=0.56 m, D=0.123 m and L₂=0.027 m, respectively. The duty cycle and the phase rising (or falling) width of the phase grating 211 are 50% and 0.375 µm. The duty cycle and the phase rising (or falling) width of the phase grating 212 are 70% and 0.375 µm. At 36 kVp tube operation voltage, the fringe visibility is estimated to be 17%. The maximally achievable interferometer sensitivity is η=7.2×10⁴. The image object position is designed to be upstream and close to the phase grating 211. Assuming the image object thickness is 8 cm, the average effective interferometer sensitivity at the object is approximately 6.5×10⁴. The field-of-view at the central plane of the image object is approximately 21 cm×17 cm.

A 2% fringe visibility degradation allows at least, for the source grating 200 or the analyzer grating 220, ±5% variation of the duty cycle; or for the phase gratings 211 or 212, ±10% variation of the grating height, or ±5% variation of the duty cycle, or ±20% variation of the phase rising (or falling) width. The grating parameters can easily be controlled to the tolerant range during the fabrication process.

What is claimed is:

1. An x-ray interferometer for x-ray phase contrast imaging, comprising:

a) an array of equally-spaced line sources with period $p_s$;
b) a phase grating $G_{p1}$ with period $p_1$ placed downstream of the array of line sources and at a distance $L_1$ from the array of line sources;
c) a phase grating $G_{p2}$ with period $p_2$ place downstream of the phase grating $G_{p1}$ at a distance D from the phase grating $G_{p1}$;
d) an analyzer grating $G_a$ formed as an absorption grating with period $p_\alpha$ and placed downstream of the phase grating $G_{p2}$ at a distance $L_2$ from the phase grating $G_{p2}$; and
e) an x-ray detector placed downstream and close to the analyzer grating $G_\alpha$; wherein
f) the period of the equally-spaced line sources $p_s$ is given by:

$$p_s = \frac{p_1 p_2 L}{(p_2 - p_1)L_2 + p_2 D}, .$$

2. The x-ray interferometer of claim 1, wherein the array of equally-spaced line sources comprises:

g) an x-ray tube source; and
h) an x-ray source grating formed as an absorption grating with the period $p_s$ placed downstream and close to the x-ray tube source.

3. The x-ray interferometer of claim 1, wherein the array of equally spaced line sources comprises of a periodically structured x-ray source.

4. The periodically structured x-ray source according to claim 3, wherein the source is generated by creating an equally spaced array of electron lines on an anode of the x-ray source.

5. The periodically structured x-ray source according to claim 3, wherein the source is generated by using a periodically structured anode.

6. The periodically structured x-ray source according to claim 3, wherein the duty cycle of the structured x-ray source is <50%, wherein the duty cycle is the ratio of the width of each individual x-ray emission element to the period $p_s$.

7. The x-ray interferometer according to claim 1, wherein $L_1$ is at least 2 times $L_2$ and the imaging object is positioned upstream and close to the phase grating $G_{p1}$.

8. The x-ray interferometer according to claim 7, wherein $L_1$ is >5 times $L_2$.

9. The x-ray interferometer according to claim 1, wherein $L_2$ is at least 2 times $L_1$, and the imaging object is positioned between the phase grating $G_{p2}$ and the analyzer grating $G_\alpha$.

10. The x-ray interferometer according to claim 9, wherein $L_2$ is >5 times $L_1$.

11. The x-ray interferometer according to claim 1, wherein the analyzer grating period $p_\alpha$ is given by:

$$p_a = \frac{p_1 p_2 (L_1 + D + L_2)}{(p_1 - p_2)L_1 + p_1 D}.$$

* * * * *